United States Patent
Mayrhofer et al.

(10) Patent No.: US 6,818,423 B2
(45) Date of Patent: Nov. 16, 2004

(54) PROCESS FOR THE PREPARATION OF CHIRAL α-HYDROXYCARBOXYLIC ACIDS

(75) Inventors: Herbert Mayrhofer, Engerwitzdorf (AT); Rudolf Neuhofer, Mittertreffling (AT); Peter Poechlauer, Linz (AT); Wolfgang Skranc, Vienna (AT); Irma Wirth, Enns (AT)

(73) Assignee: DSM Fine Chemicals Austria NFG GmbH & Co KG, Linz (AU)

( * ) Notice: Subject to any disclaimer, the term of this patent is extended or adjusted under 35 U.S.C. 154(b) by 43 days.

(21) Appl. No.: 10/286,892

(22) Filed: Nov. 4, 2002

(65) Prior Publication Data

US 2003/0092142 A1 May 15, 2003

(30) Foreign Application Priority Data

Nov. 7, 2001 (AT) .......................... 1748/2001

(51) Int. Cl.$^7$ ............................ C12P 7/42; C07C 59/00
(52) U.S. Cl. ............................ 435/146; 562/579
(58) Field of Search ............................ 435/146; 562/579

(56) References Cited

FOREIGN PATENT DOCUMENTS

GB          0100172 A1 * 2/1984

* cited by examiner

*Primary Examiner*—Paul A. Zucker
(74) *Attorney, Agent, or Firm*—Wenderoth, Lind & Ponack, L.L.P.

(57) ABSTRACT

A process for the preparation of chiral α-hydroxycarboxylic acids:

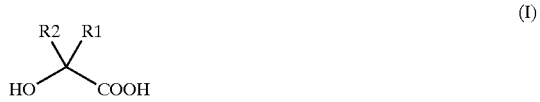

(I)

in which R1 is optionally halogen substituted $C_1$–$C_2$-alkyl and R2 is optionally halogen substituted $C_2$–$C_3$-alkyl from a compound:

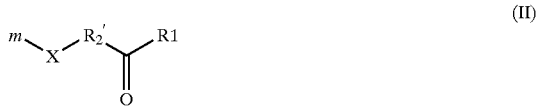

(II)

in which $R'_2$ is optionally halogen substituted $C_2$–$C_3$-alkylene, m is 0 or 1 and R is optionally substituted alkyl, aryl, heteroaryl or heterocyclyl and X can be oxygen, sulfur, sulfinyl, sulfonyl, imino, $C_1$–$C_6$-alkylimino, xanthate, silyl, or, if m is equal to 0, halogen,
which is reacted in the presence of a cyanide group donor to give the corresponding (R)- or (S)-cyanohydrin or its racemate:

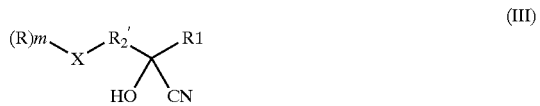

(III)

which then is converted by means of acidic hydrolysis into an acid:

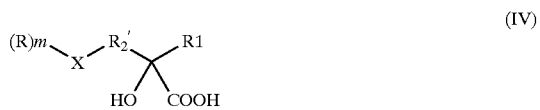

(IV)

or its racemate, and by cleavage of the group:

(R)m-X      (V), and optional resolution, whereby the desired chiral α-hydroxycarboxylic acid of the formula (I) is obtained.

8 Claims, No Drawings

PROCESS FOR THE PREPARATION OF CHIRAL α-HYDROXYCARBOXYLIC ACIDS

The invention relates to a process for the preparation of chiral α-hydroxycarboxylic acids, which are valuable intermediates for pharmaceutical and agrochemical products, from $C_4$–$C_6$-ketones.

α-Hydroxycarboxylic acids, such as, for example, 2-hydroxy-2-methyl-3-phenylthiopropionic acid, are employed, for example according to EP 0 100 172, in the preparation of acylanilides, which have anti-androgenic activity. According to EP 0 100 172, these α-hydroxycarboxylic acids are obtained as a racemate by reaction of the appropriate phenylthioketones with KCN to give the corresponding cyanohydrin and subsequent reaction with aqueous HCl. Yields, purities, and details of the configuration can be taken from EP 0 100 172.

Phenylthioketones which can serve as a precursor for the above reaction, such as, for example, 4-phenylthio-2-butanone, are obtained, for example according to J. Org. Chem. 1995, 60, 2022–2025, by addition of thiophenol to methyl vinyl ketone.

According to J. Org. Chem. 1990, 55, 4643–4647, racemic tert-α-benzyloxy acid esters are in each case cleaved into the corresponding (+)-tert-α-benzyloxy acid ester and the corresponding (S)-α-benzyloxycarboxylic acid by means of lipase OF from *Candida cylindracea*. The desired chiral α-hydroxycarboxylic acids, such as, for example, (S)-2-hydroxy-2-methyl-butyric acid, are then obtained from the (S)-α-benzyloxycarboxylic acids by hydrogenation. The yield in this process is 67%. The ee value of the final product is only 60%.

The object of the present invention was to find a process for the preparation of short-chain $C_4$–$C_6$-α-hydroxycarboxylic acids which makes possible the preparation of the desired products in high yield and enantiomeric purity.

Unexpectedly, it was possible to achieve this object by means of a process in which low-molecular-weight $C_4$–$C_6$-ketones derivatized with a chemically removable group are converted into the corresponding α-hydroxycarboxylic acids by reaction with a cyanide group donor in the presence of a hydroxynitrile lyase or by racemic reaction, subsequent acidic hydrolysis, optionally resolution, and cleavage of the group.

The invention accordingly relates to a process for the preparation of chiral α-hydroxycarboxylic acids of the formula (I)

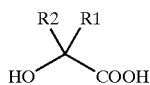
(I)

in which R1 is a $C_1$–$C_2$-alkyl radical optionally substituted by one or more halogen atoms and R2 is a $C_2$–$C_3$-alkyl radical optionally substituted by one or more halogen atoms, which comprises reacting a compound of the formula (II),

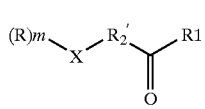
(II)

in which R1 is as defined above, $R_2'$ is a $C_2$–$C_3$-alkylene radical optionally substituted by one or more halogen atoms, m can be equal to 0 or 1, R is a $C_1$–$C_{20}$-alkyl radical, a $C_5$–$C_{20}$-aryl radical, heteroaryl radical or a heterocyclyl radical, where the radicals can optionally be mono- or polysubstituted by substituents from the group consisting of $C_1$–$C_4$-alkyl, $C_1$–$C_4$-alkoxy, $C_1$–$C_6$-alkylthio, phenyl, benzyl, halogen, hydroxyl, nitro, carboxyl, esters, thioesters, carbonates, carbamates or urethanes, and X can be oxygen, sulfur, sulfinyl, sulfonyl, imino, $C_1$–$C_6$-alkylimino, xanthate, silyl, or, if m is equal to 0, halogen, in the presence of a cyanide group donor either enantioselectively with an (R)- or (S)-hydroxynitrile lyase in an organic, aqueous or 2-phase system or in emulsion to give the corresponding (R)- or (S)-cyanohydrin of the formula (III)

(III)

in which R1, $R_2'$, R, m and X are as defined above, or racemically to give the corresponding racemate of the cyanohydrin of the formula (III), then converting the compound of the formula (III) or its racemate by means of acidic hydrolysis into the corresponding acid of the formula (IV)

(IV)

in which R1, $R_2'$, R, m and X are as defined above, or its racemate, whereupon the elimination of the group of the formula (V)

(R)m-X  (V)

takes place, where in the case of the racemate a resolution is first carried out, and isolating the desired chiral α-hydroxycarboxylic acid of the formula (I).

In the process according to the invention, chiral α-hydroxycarboxylic acids of the formula (I)

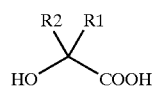

are prepared.

In the formula (I), R1 is a $C_1$–$C_2$-alkyl radical optionally substituted by one or more halogen atoms from the group consisting of fluorine, chlorine, bromine, iodine, such as, for example, methyl, ethyl, fluoromethyl, chloromethyl, bromomethyl, difluoromethyl, dichloromethyl, fluorochloromethyl, trifluoromethyl, trichloromethyl, pentafluoroethyl, pentachloroethyl, etc. A methyl radical optionally substituted by one to 3 fluorine or chlorine atoms is preferred, and an unsubstituted methyl radical is particularly preferred.

R2 is a $C_2$–$C_3$-alkyl radical optionally substituted by one or more halogen atoms from the group consisting of fluorine, chlorine, bromine, iodine, such as, for example, ethyl, difluoroethyl, propyl, pentafluoroethyl, etc. Preferably, R2 is an ethyl radical optionally substituted by one or more fluorine or chlorine atoms, particularly preferably an unsubstituted ethyl radical.

Preferably, in the compounds of the formula (I) R2 has one C atom more than R1.

Examples of compounds of the formula (I) are (R)- or (S)-2-hydroxy-2-methylbutanoic acid, (R)- or (S)-2- hydroxy-2-ethylpentanoic acid, (R)- or (S)-2-hydroxy-2-fluoromethylbutanoic acid, (R)- or (S)-2-hydroxy-2-chloromethylbutanoic acid, (R)- or (S)-2-hydroxy-2-difluoromethylbutanoic acid, (R)- or (S)-2-hydroxy-2-dichloromethylbutanoic acid, (R)- or (S)-2-hydroxy-2-trifluoromethylbutanoic acid, (R)- or (S)-3-difluoro-2-hydroxy-2-methylbutanoic acid, (R)- or (S)-4-difluoro-2-hydroxy-2-methylbutanoic acid, (R)- or (S)-3-difluoro-2-hydroxy-2-fluoromethylbutanoic acid, (R)- or (S)-4-difluoro-2-hydroxy-2-fluoro-methylbutanoic acid, (R)- or (S)-3-difluoro-2-difluoromethyl-2-hydroxy-butanoic acid, (R)- or (S)-4-difluoro-2-difluoromethyl-2-hydroxybutanoic acid, (R)- or (S)-3-difluoro-2-hydroxy-2-trifluoromethylbutanoic acid, (R)- or (S)-4-difluoro-2-hydroxy-2-trifluoromethylbutanoic acid, (2S,3S)-3-fluoro-2-hydroxy-2-methylbutanoic acid, (2S,3R)-3-fluoro-2-hydroxy-2-methyl-butanoic acid, (2R,3S)-3-fluoro-2-hydroxy-2-methylbutanoic acid, (2R,3R)-3-fluoro-2-hydroxy-2-methylbutanoic acid, etc.

The starting material used is the compound of the formula (II)

In the formula (II), R1 is as defined above.

$R_2'$ is a $C_2$–$C_3$-alkylene radical optionally substituted by one or more halogen atoms from the group consisting of fluorine, chlorine, bromine, iodine, such as, for example, ethylene, propylene, difluoroethylene, pentafluoroethylene, dichloroethylene, pentachloroethylene etc. Preferably, $R_2'$ is an ethylene radical optionally substituted by one or more fluorine or chlorine atoms, particularly preferably an unsubstituted ethylene radical.

m can be equal to 0 or 1 and R is a $C_1$–$C_{20}$-alkyl radical, a $C_5$–$C_{20}$-aryl radical, heteroaryl radical or a heterocyclyl radical.

Alkyl in this case is to be understood as meaning saturated or mono- or polyunsaturated, linear, branched or cyclic, primary, secondary or tertiary hydrocarbon radicals. These are $C_1$–$C_{20}$-alkyl radicals, such as, for example, methyl, ethyl, propyl, isopropyl, butyl, isobutyl, tert-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, octyl, cyclo-octyl, decyl, cyclodecyl, dodecyl, cyclododecyl etc.

$C_1$–$C_{12}$-alkyl radicals and particularly preferably $C_2$–$C_8$-alkyl radicals are preferred here.

The alkyl group can optionally be mono- or polysubstituted by substituents which are inert under the reaction conditions, from the group consisting of $C_1$–$C_4$-alkoxy, $C_1$–$C_6$-alkylthio, phenyl, benzyl, halogen, hydroxyl, nitro, carboxyl, esters, thioesters, carbonates, carbamates or urethanes.

Aryl is preferably to be understood as meaning $C_6$–$C_{20}$-aryl groups, such as, for example, phenyl, biphenyl, naphthyl, indenyl, fluorenyl etc.

The aryl group can in this case be optionally mono- or polysubstituted by substituents which are inert under the reaction conditions, from the group consisting of $C_1$–$C_4$-alkyl, $C_1$–$C_4$-alkoxy, $C_1$–$C_6$-alkylthio, phenyl, benzyl, halogen, hydroxyl, nitro, carboxyl, esters, thioesters, carbonates, carbamates or urethanes.

Heteroaryl or heterocyclyl are to be understood as meaning cyclic radicals which contain at least one S, O or N atom in the ring. These are, for example, furyl, thienyl, pyridyl, pyrimidyl, imidazolyl, thiazolyl, tetrazolyl, pyrazinyl, benzofuranyl, benzothiazolyl, quinolyl, isoquinolyl, isobenzofuryl, pyrazolyl, indolyl, isoindolyl, benzimidazolyl, purinyl, carbazolyl, oxazolyl, isoxazolyl, pyrrolyl, quinazolinyl, pyridazinyl, phthalazinyl etc.

Functional O or N groups can in this case be protected if necessary. The heteroaryl group or the heterocycle can in this case be optionally mono- or polysubstituted by the substituents already mentioned above.

Preferably, m is equal to 1 and R is a $C_5$–$C_{20}$-aryl or heteroaryl radical, such as phenyl, naphthyl, pyridyl, pyrimidinyl, benzothiazolyl, which can optionally be mono- or disubstituted by methyl, fluorine, chlorine, hydroxyl or nitro.

Particularly preferably, R is phenyl.

X in the compound of the formula (II) can be boron, oxygen, sulfur, sulfinyl (—SO—), sulfonyl (—$SO_2$—), imino (—NH—), $C_1$–$C_6$-alkylimino, xanthate (—O—CS—S—), silyl (—Si—), or, if m is equal to 0, halogen.

Preferably, X is sulfur, sulfinyl (—SO—), sulfonyl (—$SO_2$—), xanthate (—O—CS—S—) or silyl (—Si—).

Suitable starting compounds are, for example, 4-phenylthio-2-butanone, 4-phenylthio-4-difluoro-2-butanone, 4-phenylthio-3-difluoro-2-butanone, 4-phenylthio-1-fluoro-2-butanone, 4-phenylthio-1-difluoro-2-butanone, 4-phenylthio-1-trifluoro-2-butanone, 4-trimethylsilyl-2-butanone, 4-dimethylphenylsilyl-2-butanone, 4-diphenylmethylsilyl-2-butanone, 4-triphenylsilyl-butanone, 4-(9-borabicyclo[3.3.1]nonan-9-yl)-2-butanone, 4-diphenyl-borane-2-butanone, 4-benzylimino-2-butanone, 4-phenylsulfinyl-2-butanone, 4-phenylsulfonyl-2-butanone, O-(1-methylethyl) S-(3-oxybutyl) dithiocarbonate, O-(phenyl)-S-(3-oxybutyl) dithiocarbonate, etc.

The compounds of the formula (II) can be prepared from the corresponding ketones, for example analogously to J. Org. Chem. 1995, 60, 2022–2025, Khim. Tekhnol. (1980), 23(7), 836f. or analogously to Zhur. Org. Khim., 1971, 7, 2221. Compounds of the formula (II) in which X is sulfinyl or sulfonyl can also be prepared, for example, by oxidation of the corresponding compound of the formula (I) in which X is sulfur.

Preferably, the compounds of the formula (II) are prepared according to a slightly modified variant of J. Org. Chem. 1995, 60, 2022–2025.

Thus, for example, 4-phenylthio-2-butanone is prepared by reaction of thiophenol with methyl vinyl ketone in the presence of a tertiary amine, for example triethylamine, as a catalyst in a suitable solvent, such as, for example, methyl tert-butyl ether (MTBE) at 0° C.–10° C. and 4-phenylthio-2-butanone is isolated by extraction.

If, in the next step, the reaction with a cyanide group donor, the same solvent, for example MTBE, is employed, the compound of the formula (II) does not have to be completely isolated; the organic phase which contains the compound of the formula (II) can be employed directly. If, in these two steps, a different solvent is employed, it may be necessary to carry out a solvent exchange.

Preferably, in the preparation of the compound of the formula (II) the same solvent is used as in the following reaction with the cyanide group donor.

The compound of the formula (II) is then reacted with a cyanide group donor, it being possible for the reaction to be carried out enantioselectively in the presence of an (R)- or (S)-hydroxynitrile lyase (HNL) or in a racemic, base-catalyzed way, for example using Amberlyst, triethylamine, diazabicyclooctane, pyridine or another organic base. A suitable cyanide group donor is hydrocyanic acid, alkali metal cyanides or a cyanohydrin of the general formula (VI).

In the formula (VI), $R_3$ and $R_4$ independently of one another are hydrogen or an unsubstituted hydrocarbon group, or $R_3$ and $R_4$ together are an alkylene group having 4 or 5 C atoms, where $R_3$ and $R_4$ are not simultaneously hydrogen. The hydrocarbon groups are aliphatic or aromatic groups, preferably aliphatic groups. Preferably, $R_3$ and $R_4$ are alkyl groups having 1–6 C atoms; acetone cyanohydrin as the cyanide group donor of the formula (VI) is very preferred.

The cyanide group donor can be prepared according to known processes. Cyanohydrins, in particular acetone cyanohydrin, can also be purchased. Preferably, hydrocyanic acid (HCN), KCN, NaCN or acetone cyanohydrin, particularly preferably hydrocyanic acid, is employed as the cyanide group donor.

The hydrocyanic acid can in this case also be released from one of its salts such as, for example, NaCN or KCN, only shortly before the reaction and added to the reaction mixture as such or in dissolved form.

The cyanide group donor is in this case employed in a molar ratio to the compound of the formula (II) of 0.5:1 to 5:1, preferably of 0.8:1 to 4:1 and particularly preferably of 1:1 to 3:1.

The reaction can be carried out in an organic, aqueous or 2-phase system or in emulsion.

Organic diluents used can be aliphatic or aromatic hydrocarbons which are immiscible or slightly miscible with water and which are optionally halogenated, alcohols, ethers or esters or mixtures thereof. Preferably, methyl tert-butyl ether (MTBE), diisopropyl ether, dibutyl ether and ethyl acetate or a mixture thereof are employed.

In the enantioselective reaction, the aqueous system used is an aqueous solution or buffer solution containing the corresponding HNL. Examples thereof are Na citrate buffer, phosphate buffer etc.

The HNLs can be present in the organic diluent here either as such or immobilized, but the reaction can also be carried out in a two-phase system or in emulsion with nonimmobilized HNL.

Suitable HNLs are both native and recombinant (R)- and (S)-HNLs, such as are known from the prior art, for example from EP 0 969 095, EP 0 951 561, EP 0 927 766, EP 0 632 130, EP 0 547 655, EP 0 326 063, WO 01/44487 etc.

The base- or enzyme-catalyzed addition of the cyanide group to the appropriate compound of the formula (II) can in this case be carried out analogously to the prior art, for example analogously to EP 0 969 095, EP 0 951 561, EP 0 927 766, EP 0 632 130, EP 0 547 655, EP 0 326 063 etc.

The corresponding (R)- or (S)-cyanohydrin of the formula (III) or its racemate can then be hydrolyzed without further purification analogously to the prior art, for example as described in Angew. Chem. 1994, 106, p.1615 or in Tetrahedron Letters, Vol. 31, No. 9, pp 1249–1252, 1990, using concentrated hydrochloric acid, for example after extraction or, if appropriate, after filtering off the enzyme and distilling off the solvent. Other suitable acids, such as, for example, $H_2SO_4$, can also be used for the hydrolysis, but HCl is preferably employed.

The working up of the reaction solution, which contains the crude (R)- or (S)-α-hydroxycarboxylic acids which are obtained in this way and have approximately the same optical purity as the corresponding (R)- and (S)-cyanohydrins, can then be carried out either directly or after dilution of the resulting reaction solution with water and subsequent extraction with MTBE, toluene, xylene, (poly) ethers, halogenated hydrocarbons, acetonitrile etc. between 10–99° C., preferably between 15–95° C. and particularly preferably between 20–90° C. Preferably, toluene or xylene is used here.

To achieve an enrichment of the desired enantiomer, the extraction solution is preferably concentrated and strongly cooled down to −10° C. After this, the resulting crystals are separated off, for example by means of a suction filter, recrystallized, preferably in an aromatic hydrocarbon, if appropriate in the presence of a cosolvent and the product is obtained with a higher ee than in the cyanohydrin stage.

Further, it is possible to couple the crystallization step directly to the hydrolysis step so that the extraction of the hydroxycarboxylic acid by means of ethers is unnecessary. To this end, an aromatic hydrocarbon, if appropriate in combination with a cosolvent, is added to the hydrolysis solution at hydrolysis temperature and the reaction mixture is extracted. The aqueous phases are discarded, whereupon the combined organic phases are cooled, preferably after concentration, and the highly pure hydroxycarboxylic acids crystallize out.

If the racemate of the α-hydroxycarboxylic acid (IV) is obtained, resolution with a cleavage base is first carried out. Suitable cleavage bases are, for example, chiral amines, for example those such as are described, for example, in T. Vries et al., Angew. Chem., Int. Ed., (1998), 37, pp 2349–2354, such as, for example, (R)- or (S)-phenylethylamine, (L)- or (D)-phenylglycinamide, (L)- or (D)-norephedrine, (R)- or (S)-naphthylethylamine etc.

The cleavage is carried out in a solvent in which the α-hydroxycarboxylic acid dissolves, for example in isopropyl acetate (IPA), ethyl acetate, toluene, xylene. After the addition of the cleavage base, crystallization is begun by cooling the reaction mixture with stirring. In the crystallization, it is also possible to assist or induce this by seeding. Cooling down to −15° C. is carried out, preferably down to approximately +10° C. After crystallization is complete, the mixture is filtered, and the crystals are optionally washed and optionally then dried.

To release the corresponding chiral acid, HCl is then added to a mixture of chiral salt, water and a suitable solvent, whereby two clear phases are obtained. Suitable solvents are those which are immiscible with water, which dissolve the acid and which are resistant to HCl. Examples thereof are ethers and hydrocarbons. Preferably, ethers are employed, particularly preferably MTBE.

If the corresponding enantiomerically enriched α-hydroxycarboxylic acid is then present in purified form, the cleavage of the chemically removable group of the formula (V) is carried out.

This is carried out, for example, in the case where X=S and derivatives thereof by means of Raney Ni, $NiCl_2$ and $NaBH_4$, $Cl_2$, resulting halides having to be removed, for example, by means of zinc, such as, for example, analogously to J. Org. Chem., Vol. 58, No. 9, 1993, 2407–2413. If X=O, the group RmO can be removed by elimination, an unsaturated α-hydroxycarboxylic acid in this case being formed by elimination, which optionally has to be hydrogenated.

If X=Si, the group RmSi can be removed by basic work-up ($K_2CO_3$ in methanol), by treatment with fluoride ions (KF, NaF) or conc. HCl for a number of hours.

By means of the process according to the invention, chiral α-hydroxycarboxylic acids are obtained from $C_4$–$C_6$-ketones in high yields and in high enantiomeric purity, it being possible for the enantioselective HCN addition to proceed significantly more selectively than according to the prior art and for the resolution after the racemic HCN addition needing to be carried out using simpler resolving reagents than according to the prior art.

EXAMPLE 1

Preparation of the compound of the formula (II) (4-phenylthio-2-butanone) analogously to J. Org. Chem. 1995, 60, 2022–2025

113.5 g (1.03 mol) of thiophenol and 1.0 g (9.8 mmol) of triethylamine were introduced into 250 ml of MTBE at 0° C. 70.1 g (1.03 mol) of methyl vinyl ketone were added dropwise to this cold solution in the course of one hour so that the temperature was kept between 0–10° C. The reaction mixture was then stirred at 10° C. for 1 hour. The reaction solution was treated with a further 250 ml of MTBE and extracted with 200 ml of 4% NaOH solution. The MTBE phase was extracted with 200 ml of conc. NaCl solution and then concentrated to dryness.

Yield: 164.6 g of 4-phenylthio-2-butanone (91.3% of theory)

EXAMPLE 2

Preparation of the compound of the formula (III) ((S)-2-hydroxy-2-methyl-4-phenylthiobutyronitrile)

11.35 g of thiophenol and 0.1 g of triethylamine were introduced into 25 ml of MTBE at 0° C. 7.01 g of methyl vinyl ketone were added dropwise to this cold solution in the course of one hour so that the temperature was kept between 0–10° C. The reaction solution was then stirred at 10° C. for 2 hours. The reaction solution was then treated with a further 25 ml of MTBE and extracted with 25 ml of 4% NaOH solution. The organic phase was extracted with 25 ml of dist. water and then treated with 50 ml of buffer solution ($K_2HPO_4$/citrate 30 mmol, pH 6.0) and stirred for 10 min. The pH of the two-phase mixture was adjusted to pH 6.0 using 10% strength aqueous citric acid.
4.5 ml of S-HNL from *Hevea brasiliensis* (6930 IU/ml) were added to this two-phase mixture and this reaction mixture was beaten to an emulsion at 0° C. After this, 8.0 ml of HCN were added at 0° C. in the course of 1 hour. After stirring for a further 3 hours, 50 ml of MTBE were admixed to the reaction solution, it was stirred for 10 min and the phases were separated. The aqueous phase was extracted again with 25 ml of MTBE and the combined organic phases were freed of the solvent on a Rotavapor.

Yield: 17.3 g of 2-hydroxy-2-methyl-4-phenylthiobutyronitrile (88.13% of theory), 94.09% ee The ee value was determined on a CP-Chirasil-Dex-CB column, the cyanohydrin being derivatized using 1-trimethylsilylimidazole in dichloromethane.

EXAMPLE 3

Preparation of the compound (S)-2-hydroxy-2-methyl-4-phenylthiobutyric acid 100.0 g (0.509 mol) of (S)-2-hydroxy-2-methyl-4-phenylthiobutyronitrile (ee: 95.45%) were added to 800 ml of conc. HCl at 65° C. and the mixture was stirred for 90 min. After this, the temperature was increased to 85° C. and the mixture was allowed to react at this temperature for 120 min. After this, 200 ml of toluene were added at 85° C. and the mixture was stirred at 50° C. for 15 min. After the phase separation, the organic phase was stripped off and the aqueous phase was extracted again with 50 ml of toluene. The combined organic phases were cooled to 0° C. with addition of 100 ml of toluene (for the purpose of easier filterability). The deposited crystals were filtered off and dried.

Yield: 55.2 g of (S)-2-hydroxy-2-methyl-4-phenylthiobutyric acid (47.9% of theory), >99.0% ee

EXAMPLE 4

Synthesis of racemic (R/S)-2-hydroxy-4-phenylthiobutyronitrile 9.01 g (50 mmol) of 4-phenylthio-2-butanone were dissolved in 30 ml of MTBE and treated with 1.0 g of ion exchanger Amberlyst A-21. After this, 9.8 ml (250 mmol) of HCN were added with stirring and the mixture was stirred at room temperature for 2 hours. The ion exchanger was filtered off and 0.05 g of citric acid was added to the solution. The solvent and HCN were stripped off in vacuo at 40° C. on a rotary evaporator. 9.5 g of (R/S)-2-hydroxy-4-phenylthiobutyronitrile (91.7% of theory) were found.

EXAMPLE 5

Synthesis of rac-2-hydroxy-2-methyl-4-phenylthiobutyric acid 7.75 g (39.5 mmol) of rac-2-hydroxy-2-methyl-4-phenylthiobutyronitrile, prepared according to example 4, were treated with 77.5 g of conc. HCl and stirred at 65° C. until the disappearance of the cyanohydrin. The temperature was then increased to 85° C. and the mixture was stirred for 6 hours. The batch was treated with 100 ml of water, cooled to room temperature and extracted three times with MTBE. The combined organic phases were dried over $Na_2SO_4$ and evaporated to dryness. The crude product was digested using heptane.

Yield: 6.80 g of rac-2-hydroxy-2-methyl-4-phenylthiobutyric acid (80.3% of theory)

EXAMPLE 6

Resolution 5.00 g (22.1 mmol) of rac-2-hydroxy-2-methyl-4-phenylthiobutyric acid, prepared according to example 5, were dissolved in ethyl acetate (60° C.) and treated with 2.67 g (22.1 mmol) of S-(−)-phenylethylamine. One third volume of ethyl acetate to DIPE was then added. On cooling, the mixture was seeded using seed crystals so that, after cooling to 10° C., the diastereomeric salt of S-phenylethylamine and R-2-hydroxy-2-methyl-4-phenylthiobutyric acid crystallized out. The salt was filtered off with suction, boiled in hydrochloric acid and extracted with MTBE. The organic phase was stripped off and R-2-hydroxy-2-methyl-4-phenylthiobutyric acid was obtained in an R/S ratio of over 3:1 and a yield of 80%.

EXAMPLE 7

Synthesis of (S)-2-hydroxy-2-methylbutyric acid 25.0 g (0.110 mmol) of (S)-2-hydroxy-2-methyl-4-phenylthiobutyric acid (99.4% ee), prepared analogously to example 3, were dissolved in 55.2 ml of 2 M sodium hydroxide solution and heated to 70–74° C. under an argon atmosphere. 190.0 g of Raney Ni were then added in portions in the course of 2 hours and the mixture was subsequently stirred at 70–74° C. for 3 hours. The catalyst was filtered off and washed with water. The filtrate was extracted once with MTBE. The aqueous phase (pH 9.8) was acidified to pH 1 using conc. HCl and extracted three times with MTBE, being salted out with NaCl. The combined organic phases were dried using sodium sulfate and evaporated to dryness.

12.21 g of crude product were recrystallized from 400 ml of n-hexane.

Yield: 11.6 g of (S)-2-hydroxy-2-methylbutyric acid (99.4% ee) (88.9% of theory)

EXAMPLE 8

Synthesis of (S)-2-hydroxy-2-methylbutyric acid 5.0 g (2.20 mmol) of (S)-2-hydroxy-2-methyl-4-phenylthiobutyric acid (99.0% ee), prepared according to example 3, were dissolved in 44 ml of methanol/tetrahydrofuran (3:1) and treated with 23.6 g of $NiCl_2$. The green solution was cooled to 3° C. and treated with 11.3 g of sodium borohydride between 10–25° C. in the course of 180 min and stirred overnight. 2.6 g of $NiCl_2$ in 20 ml of methanol/tetrahydrofuran (3:1) were then added and 1.3 g of $NaBH_4$ were introduced in the course of 30 min at a maximum of 20° C. The solution was evaporated, 30 ml of water being added. After addition of 30 ml of semiconcentrated HCl and 30 ml of MTBE, the precipitate was filtered off after some time, the two-phase mixture was treated with $NaCl^-$ and the phases were separated. The aqueous phase was extracted a further two times with MTBE. The combined organic phases were dried using sodium sulfate and evaporated to dryness.

Yield: 2.33 g of (s)-2-hydroxy-2-methylbutyric acid (97.6% ee) (89.2% of theory)

What is claimed is:

1. A process for the preparation of chiral α-hydroxycarboxylic acids of the formula (I)

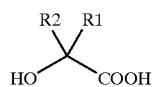

(I)

in which R1 is a $C_1$–$C_2$-alkyl radical optionally substituted by one or more halogen atoms and R2 is a $C_2$–$C_3$-alkyl radical optionally substituted by one or more halogen atoms, which comprises reacting a compound of the formula (II)

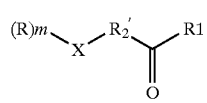

(II)

in which R1 is as defined above, $R_2'$ is a $C_2$–$C_3$-alkylene radical optionally substituted by one or more halogen atoms, m can be equal to 0 or 1, R is a $C_1$–$C_{20}$-alkyl radical, a $C_5$–$C_{20}$-aryl radical, heteroaryl radical or a heterocyclyl radical, where the radicals can optionally be mono- or polysubstituted by substituents from the group consisting of $C_1$–$C_4$-alkyl, $C_1$–$C_4$-alkoxy, $C_1$–$C_6$-alkylthio, phenyl, benzyl, halogen, hydroxyl, nitro, carboxyl, esters, thioesters, carbonates, carbamates or urethanes, and X can be oxygen, sulfur, sulfinyl, sulfonyl, imino, $C_1$–$C_6$-alkylimino, xanthate, silyl, or, if m is equal to 0, halogen, in the presence of a cyanide group donor either enantioselectively with (R)- or (S)-hydroxynitrile lyase in an organic, aqueous or 2-phase system or in emulsion to give the corresponding (R)- or (S)-cyanohydrin of the formula (III)

(III)

in which R1, $R_2'$, R, m and X are as defined above, or racemically to give the corresponding racemate of the cyanohydrin of the formula (III), then converting the compound of the formula (III) or its racemate by means of acidic hydrolysis into the corresponding acid of the formula (IV)

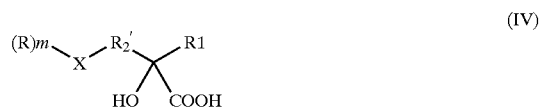

(IV)

in which R1, $R_2'$, R, m and X are as defined above, or its racemate, whereupon the cleavage of the group of the formula (V)

(V)

is carried out, where in the case of the racemate a resolution is first carried out, and isolating the desired chiral α-hydroxycarboxylic acid of the formula (I).

2. The process as claimed in claim 1, wherein, in the formula (I), R1 is a methyl radical optionally substituted by one to three fluorine or chlorine atom and R2 is an ethyl radical optionally substituted by one to three fluorine or chlorine atoms and, in the formula (II), R1 is a methyl radical optionally substituted by one to three fluorine or chlorine atoms, $R_2'$ is an ethylene radical optionally substituted by one to three fluorine or chlorine atoms, m is equal to 1, R can be a $C_5$–$C_{20}$-aryl radical or heteroaryl radical, which can optionally be mono- or disubstituted by methyl, fluorine, chlorine, hydroxyl or nitro, and X and is sulfur, sulfinyl, sulfonyl, xanthate or silyl.

3. The process as claimed in claim 1, wherein the cyanide group donor is hydrocyanic acid, alkali metal cyanides or a cyanohydrin of the formula

(VI)

in which $R_3$ and $R_4$ can independently of one another be hydrogen or an unsubstituted aliphatic or aromatic hydrocarbon group, or $R_3$ and $R_4$ together are an alkylene group having 4 or 5 C atoms, where $R_3$ and $R_4$ are not simultaneously hydrogen.

4. The process as claimed in claim 1, wherein the organic solvents used are aliphatic or aromatic hydrocarbons which are immiscible or slightly miscible with water and which are optionally halogenated, alcohols, ethers or esters or mixtures thereof, or wherein, in the enantioselective reaction, the aqueous system used is an aqueous solution or buffer solution containing the appropriate hydroxynitrile lyase.

5. The process as claimed in claim 1, wherein the enantioselective reaction, both native and recombinant (R)- and (S)-hydroxynitrile lyases can be employed.

6. The process as claimed in claim 1, wherein the (R)- or (S)-cyanohydrin of formula (III) is hydrolyzed using HCl or $H_2SO_4$, the reaction solution is extracted at 10 to 99° C. with a suitable extracting agent selected from the group consisting of methyl tert-butyl ether, toluene, xylene, (poly)ethers, halogenated hydrocarbons or acetonitrile, optionally after dilution with water, the extraction solution is cooled to −10° C. and the resulting crystals of the corresponding (R)- or (S)-α-hydroxycarboxylic acids of the formula (IV) are separated off and optionally recrystallized in an aromatic hydrocarbon, optionally in the presence of a cosolvent.

7. The process as claimed in claim 1, wherein racemic cyanohydrin of the formula (III) is hydrolyzed using HCl or $H_2SO_4$, the reaction solution is extracted at 10 to 99° C. with a suitable extracting agent from the group consisting of methyl tert-butyl ether, toluene, xylene, (poly)ethers, halogenated hydrocarbons or acetonitrile, optionally after diluting with water, whereupon the racemate of the α-hydroxycarboxylic acids of the formula (IV) is cleaved using a chiral amine as a cleavage base in a solvent in which the hydroxycarboxylic acid dissolves, and the corresponding chiral salt is crystallized out, which is treated with HCl in water and a suitable organic solvent for the release of the corresponding chiral acid.

8. The process as claimed in claim 1, wherein the cleavage of the group of the formula (V) wherein X is sulfur and its derivatives is carried out by means of Raney Ni, $NiCl_2$ and $NaBH_4$ or chlorine, wherein halides as by-products result and are removed, or with X equal to oxygen by elimination, whereby an unsaturated α-hydroxycarboxylic acid is obtained, which can optionally be hydrogenated, or with X equal to Si, by basic work-up, by treatment with fluoride ions or by means of HCl.

* * * * *